United States Patent [19]

Laughlin et al.

[11] Patent Number: 5,399,404
[45] Date of Patent: Mar. 21, 1995

[54] FOOT AND SHOE DEODORIZER PATCH

[75] Inventors: Thomas J. Laughlin, Germantown; Gerald R. Dever, Cordova, both of Tenn.

[73] Assignee: Schering-Plough Healthcare Products, Memphis, Tenn.

[21] Appl. No.: 106,962

[22] Filed: Aug. 16, 1993

Related U.S. Application Data

[63] Continuation of Ser. No. 810,618, Dec. 19, 1991, abandoned.

[51] Int. Cl.$^6$ ............................................. B32B 9/00
[52] U.S. Cl. .................................... 428/40; 428/42; 428/43; 428/68; 428/78; 428/201; 428/224; 428/304.4; 428/321.5; 428/327; 428/343; 428/352; 428/354; 428/402.2; 428/402.21; 428/522; 428/905; 239/34; 239/36; 239/54
[58] Field of Search .............. 428/343, 76, 280, 224, 428/246, 905, 225, 247, 40, 42, 43, 68, 63, 78, 201, 304.4, 321.5, 327, 352, 354, 355, 402.2, 402.21, 522; 239/34, 54, 36

[56] References Cited

U.S. PATENT DOCUMENTS

| | | |
|---|---|---|
| 4,161,284 | 7/1979 | Rattan . |
| 4,283,011 | 8/1981 | Spector . |
| 4,284,444 | 8/1981 | Bernstein et al. .................. 156/60 |
| 4,735,010 | 4/1988 | Grinarml .............................. 43/1 |
| 4,880,690 | 11/1989 | Szycher et al. ..................... 428/224 |

FOREIGN PATENT DOCUMENTS

| | | |
|---|---|---|
| 0272690A2 | 6/1988 | European Pat. Off. . |
| 0300084A2 | 1/1989 | European Pat. Off. . |
| 1455904A | 10/1966 | France . |
| 451950 | 10/1927 | Germany . |
| 1718084 | 10/1955 | Germany . |
| 3233006A1 | 3/1984 | Germany . |
| 3516653A1 | 11/1986 | Germany . |
| 2183479A | 6/1987 | United Kingdom . |
| WO90/04339 | 5/1990 | WIPO . |

OTHER PUBLICATIONS

Robert T. Maleeny and William F. Palmer, Environmental Odor Control, Soap/Cosmetics/Chemical Specialties for Jan. 1991, pp. 28–31.

F. Kanda, et al., British Journal of Dermatology, 122, (1990), pp. 771–776.

The Handbook of Water-Soluble Gums and Resins by Robert L. Davidson, Chapter 21—"Polyvinylpyrrolidone", McGraw-Hill, Inc. (1980), pp. 21-1 to 21-21.

Primary Examiner—Patrick J. Ryan
Assistant Examiner—Abraham Bahta
Attorney, Agent, or Firm—Joseph T. Majka; Eric S. Dicker

[57] ABSTRACT

A patch for masking foot and shoe odors through controlled release of fragrance is claimed.

14 Claims, 1 Drawing Sheet

FOOT AND SHOE DEODORIZER PATCH

This is a continuation, of application Ser. No. 07/810,618, filed Dec. 19, 1991, now abandoned.

FIELD OF THE INVENTION

The present invention relates to a patch for masking foot and shoe odors through controlled release of fragrance.

BACKGROUND

According to Robert T. Maleeny and William F. Palmer, Environmental Odor Control, Soap/Cosmetics/Chemical Specialties for January 1991, pp. 28-31, malodors are usually caused by chemicals that are perceived at very low concentrations. Although malodors may not be dangerous to health at low levels, they can affect one's enjoyment of the environment. Maleeny and Palmer disclose that the perfumers of ancient Egypt and Medieval Europe practised masking by deodorizing through the use of perfumes, colognes and sachets. The authors also suggested that foot care can be one of many applications for malodor counteractants.

F. Kanda et al, British Journal of Dermatology, 122, (1990), pp. 771-776 found that short-chain fatty acids, particulary iso-valeric acid, are largely responsible for foot malodour.

U.S. Pat. No. 2,973,286 discloses solvent resistant, pressure-sensitive tape adhesive coatings derived from copolymers of (a) certain monomeric acrylic acid esters of non-tertiary alkyl alcohol and (b) small proportions of certain copolymerizable monomers formed by heating the acrylate copolymers with small proportions of benzoyl peroxide or other organic peroxide soluble in the copolymer. However, U.S. Pat. No. 2,973,286 fails to suggest the use of this adhesive for the skin and in association with fragrances.

U.S. Pat. No. 4,051,159 discloses a shaped, self-supporting transparent article capable of emitting fragrance over a sustained period made of a polyamide resin formed from a polymerized fatty carboxylic acid and a polyamine, a C-14 to C-22 alkyl alcohol and a volatile essential oil.

U.S. Pat. No. 4,284,444 discloses non-porous, polymeric articles having active compounds such as antibacterial, antifungal, pesticidal, insecticidal, animal repellent, odorous, antistatic and the like, by applying to a surface of the article selected activating agents which are capable of migrating or moving throughout the body of the article to impart an effective level of activity throughout the article and/or on a surface other than the one to which the activating agents have been applied.

U.S. Pat. No. 4,419,396 discloses a three-dimensional perfumed seal made of a vinyl base sheet, an adhesive layer applied to one surface of the base sheet, a relese paper applied to the surface of the adhesive layer opposite from the base sheet, a foam synthetic resin padding material disposed on the surface of the base sheet opposite from the the adhesive layer, a covering vinyl sheet sandwiching ther padding material in cooperation with the base sheet and having a design printed on one of the opposite surfaces, and a capsulated perfume layer laminated to the covering vinyl sheet at the area where the design is present.

U.S. Pat. No. 4,493,869 discloses a flexible substrate which is transparent or translucent and which has on one surface a coating made of a binder resin having rupturable microcapsules dispersed therein and on the other surface a pressure sensitive or water-activated adhesive. The microcapsules can contain fragrances.

U.S. Pat. No. 4,605,592 and European Patent Application 103,407 disclose a multilayer decorative article having in order, an ink receptive vinyl film layer, a plasticizer barrier layer, and a pressure-sensitive adhesive layer, the adhesive layer being adapted to maintain adhesion to highly plasticized vinyl substrates, and the intermediate barrier layer being capable of preventing plasticizer from migrating from the vinyl substrate into the vinyl film outer layer.

PCT International Publication No. WO 79/01013 discloses pressure-sensitive tape adhesive made of a copolymer of alkyl acrylate and copolymerizable acid such as acrylic acid, which adhesive includes a small amount of $Cr^{3+}$ ion which crosslinks the acid groups, giving the adhesive good electrical insulating properties.

U.S. Pat. Nos. 4,654,256, 4,774,133 and 4,898,663 disclose articles comprising a thermoplastic substrate bearing rupturable, fragrance-containing microcapsules in a binder on at least one surface thereof.

U.S. Pat. Nos 4,696,844 and 4,720,409 disclose a replaceable, film type air freshener primarily for use on the tiled wall of a bathroom or kitchen in which the film is constituted by a polymeric matrix having myriad cells dispersed therein impregnated with a volatile fragrance which is slowly released from the film into the atmosphere of the room.

U.S. Pat. Nos. 4,714,655 discloses a heat-sensitive material in a pressure-sensitive-adhesive matrix formed by ultraviolet and/or EB radiation, the rate of release of which can be controlled by the degree of crosslinking employed, in which the functioning of the retainined heat-sensitive material is determined by release from the pressure-sensitive-adhesive matrix at a controlled rate, of ointments containing materials such as menthols, drugs, muscle painkillers, insect repellants or fragrances.

U.S. Pat. No. 4,735,010 discloses a scent distributing device attached to footwear, including a scent source and a tubular body.

U.S. Pat. No. 4,737,410 discloses pressure-sensitive adhesives made of blends of acrylate copolymer compositions with polylyalkyloxazolines.

U.S. Pat. Nos. 4,710,536 and 4,749,590 and European Patent Application 213,737 disclose the incorporation of hydrophobic silica into acrylic pressure-sensitive adhesive tape to improve shear strength.

U.S. Pat. No. 4,814,212 discloses a repaceable air freshener unit adapted to be adhered to an automobile window to suffuse the interior of the vehicle with a pleasing or stimulating aroma.

U.S. Pat. No. 4,874,129 discloses a multi-laminate fragrance sustained release devise for releasing fragrances, colognes and perfumes at a controlled rate having a first layer of a pressure sensitive adhesive release liner for providing a protective peel strip for the device, a second layer of a silicone pressure sensitive adhesive for adhering the device to a substrate to which it is applied including human skin, a third layer of a fragrance oil impregnated matrix of a silicone material selected from the group consisting of silicone elastomers, silicone elastomers having adhesive characteristics and elastomeric silicone pressure sensitive adhesives, and a fourth layer of a permeable facestock backing member on the surface of the device for controlling the rate of release of the fragrance oil from the impregnated matrix.

U.S. Pat. No. 4,880,690 discloses perfume-emitting article or perfume patch including a fragrance-emitting layer or member comprising a fragrance oil dispersed within an ultra-thin polyurethane membrane which may be on a support.

U.S. Pat. No. 4,889,755 discloses microencapsulated materials on a strip provided between two sheet surfaces such that upon removal of the strip from between the two surfaces, some capsules rupture, releasing material contained therein.

U.S. Pat. No. 4,943,461 discloses a photopolymerized pressure-sensitive adhesive which adheres well to all common surfaces and is capable of bonding to plasticized vinyl substrates comprising an acrylic copolymer and a nitrile butadiene rubber or mixture of rubbers.

U.S. Pat. No. 4,959,208 discloses an active agent delivery device comprising (a) microporous material comprising a matrix consisting of linear ultrahigh molecular weight polyolefin, a large porportion of finely divided water-insoluble filler of which at least about 50 percent by weight is siliceous and interconnecting pores; and (b) a releasable active agent or precursor thereof associated with at least a portion of the filler.

PCT International Application WO 89/07429 discloses a printed transdermal drug delivery device made of a backing layer, an anchor adhesive layer, a layer of a pressure-sensitive pharmaceutically acceptable contact adhesive layer, an adsorbent fibrous source layer and a drug dissolved in the anchor adhesive layer or the pressure-sensitive adhesive layer.

In an AWEAR® product specifications sheet by Thermedics Inc., 470 Wildwood Street, P.O. Box 2999, Woburn, Mass., 2 pages, is described wearable self-adhesive patches which contain essential oils which are released by heat from the skin. The patches contain acrylic adhesive with a peel adhesion of 2.0 lb @ 180°, a barrier layer of clear polyolefin film and a fragrance containing layer made of polyurethane.

Despite the extensive research in materials research, the art fails to teach a patch which can mask foot and shoe odors through controlled release of fragrance and still remain securely attached to the foot for at least 8 hours, or to the shoe for at least 24 hours to one week. Nor are any commercially available perfume patches known which can attach to the foot or shoe and can meet the above requirements. Part of the problem lies in the relatively high loading of fragrance in the patch (i.e. about 10 milligrams (mg) or greater) necessary to mask the foot and shoe odors. Such concentrated loadings of fragrance in the patch can cause the patch adhesive to soften, causing the patch to loosen from the skin or footwear. In view of the foregoing, it would be desirable to provide a convenient patch for masking foot and shoe odors and which would be easy to apply and remove, but would remain securely attached to the foot or shoe.

SUMMARY OF THE INVENTION

In one embodiment, the present invention is directed toward a modified patch for masking foot or shoe odors, comprising:
a) a non-occlusive
b) a carrier on one side of the non-occlusive layer and containing from about 10 milligrams fragrance or more per patch;
c) a pressure sensitive adhesive on the other side of the non-occlusive layer for securing said patch to a foot or shoe, such that the patch can mask foot odors through release of fragrance and still remain securely attached to the foot for at least an 8 hour period or to the shoe for at least a 24 hour period.

In another embodiment, the present invention is directed toward a patch for masking foot or shoe odors, comprising:
a) a non-occlusive layer
b) a carrier on one side of the non-occlusive layer and containing from about 10 milligrams fragrance or more per patch;
c) a pressure sensitive adhesive on the other side of the non-occlusive layer for securing said patch to a foot or shoe,
wherein said adhesive is a polyisobutylene-based adhesive or the adhesive is the reaction product of reactants comprising
  (i) acrylic acid and/or methacrylic acid and/or acrylamide, and/or methacrylamide,
  (ii) an alkylacrylate and/or alkylmethacrylate having at least 4 carbon atoms and wherein the carbon atom attached to the oxy atom of the carbonyloxy group has at least one hydrogen atom attached thereto, and
  (iii) at least one additional ethylenically unsaturated monomer. Preferably the adhesive is a terpolymer prepared from acrylic acid, n-butyl or iso-octyl acrylate or methacrylate and N-vinyl pyrrolidone.

Also preferred is that the adhesive is derived from polyisobutylene (PIB), polybutene and a tackifier.

In a more preferred embodiment, the present invention further comprises
d) a release liner in contact with said skin adhesive for preventing contamination of the adhesive prior to contact with the foot or shoe.

The present invention has the advantage of masking undesirable odors in a shoe by the controlled release of fragrance lasting over a normal day's wear. A second advantage is that in one embodiment, the controlled fragrance release can be triggered by moisture from the foot, thus minimizing fragrance loss from the patch prior to application to the foot or footwear. In a preferred embodiment where a felt carrier is employed, a third advantage of present invention is that it reduces the tackiness at the exposed surface of the patch due. A fourth advantage of the present invention is that the patch is easy to apply and remove, but will remain secured to the foot or shoe being worn. A fifth advantage of the present patch is that it will stay secured to the foot or shoe even when the patch is moistened or made wet. A sixth advantage is that the present patch will remain securely adhered to the foot or shoe, despite the shear forces imposed upon it by the foot in contact with the shoe during walking or running.

DETAILED DESCRIPTION OF THE FIGURES

Figure 1:
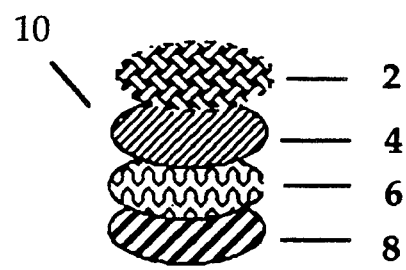

FIG. 1 illustrates an exploded view of circular perfume patch 10 made of carrier 2, barrier layer 4, adhesive 6 and release liner 8. To one side of non-occlusive layer 4 is carrier 2 made of felt whose fibers are coated with a polymer containing a fragrance of choice. Skin or shoe adhesive 6 is attached to the other side of non-occlusive layer 4. Adhesive 6 is covered with release liner 8. Carrier 2 can be adhered to non-occlusive layer 4 by a permanent adhesive or by scintering (i.e. heating). Non-occlusive layer 4 serves to minimize interaction between adhesive 6 and the fragrance in carrier 2.

Figure 2:
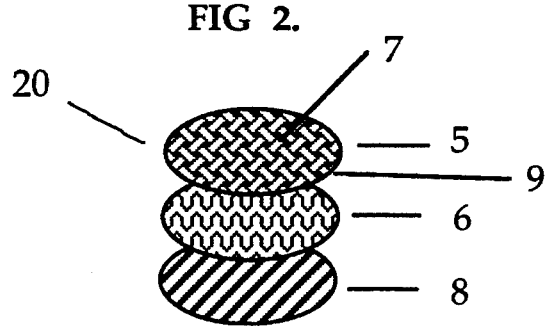

FIG. 2 represents an exploded view of perfume patch 20 made of a felt carrier/non-occlusive layer 5 in which the carrier and barrier is integrally bound. Carrier/non-occlusive layer 5 is sintered on underside 9 to form a non-occlusive. Exterior side 7, which is not sintered, of carrier/non-occlusive layer 5 is coated with a polymer and fragrance. Skin or shoe adhesive 6 is attached to sintered underside 9 of carrier/non-occlusive layer 5. Release liner 8 covers adhesive 6.

DETAILED DESCRIPTION OF THE INVENTION

For purposes of this invention, the term "shoe" includes any article of footwear to which the patch can be attached, such as men's and women's shoes, sneakers, athletic footwear, sandals and the like.

The non-occlusive layer in the patch should be made from materials which can help separate the fragrance in the carrier from the adhesive to minimize their interaction, i.e. softening. The non-occlusive layer can also provide additional strength to the patch for wearing and for manufacturing, as well as anchorage for the carrier and for the adhesive. Generally, the non-occlusive layer is a component separate and discrete from the carrier. However, the non-occlusive layer can also be an integral part of the carrier, such as by foaming or polymerizing certain polymers directly onto the carrier surface, or by sintering one side of the felt.

For patches to be worn on the foot, the non-occlusive layer generally should be flexible. The term "non-occlusive" refers to the ability of a material to block or reduce the rate of transport of a specified material. For example, the non-occlusive layer of a foot patch should be non-occlusive to the transport of moisture. A non-occlusive barrier allows the patch to "breathe", thus preventing maceration of the skin due to accumulation of moisture. For certain polymers, the barrier layer can be foamed or polymerized directly onto the carrier surface. Preferably, the non-occlusive layer is a carrier felt made of thermoplastic fibers, such as polypropylene fibers, in which one side of the felt is sintered to form a non-occlusive, layer. The thickness of the non-occlusive layer can range from 0.5 to about 10 mils, preferably about 1 mil.

For patches to be worn on the shoe, the barrier layer for footwear can be non-occlusive. For example, the barrier layer for footwear can include continuous or discontinuous polymer films of low density polyethylene, polypropylene, polyurethanes, polyacrylics, polymer films of polyesters i.e. terephthalate (mylar), polyvinylidene and polyvinyl chloride.

The carrier is the structural component of the patch which supports or carries the fragrance and/or polymer. Optionally, the carrier can be integrally bound to the barrier layer. The carrier can be made of fibrous materials including polypropylene felt, woven and non-woven materials, fabrics, microporous membranes (diffusion loaded), fused microcapsules (encapsulated), monolith films (cast blends of polymer and fragrance) or films of polymers which form molecular associations with the fragrance. Suitable microporous membranes include microporous polyethylene films into which fragrances are diffusion loaded. Preferably, the carrier is a non-woven felt of polypropylene fibers forming a thickness of about 20 to about 60 mils thickness, preferably about 35 mils thickness. A felt carrier has the advantage of being able to reduce the oily feel imparted by the fragrance as well as providing enhanced surface area for coating with fragrance/polymer matrices. Also preferred is that the carrier is coated with selected polymer/fragrance blends. The carrier can be bonded to the non-occlusive layer with a permanent adhesive or can be directly sintered on one side to form the non-occlusive layer.

Fragrances employed in the present patch can include any commercial or proprietary fragrance, preferably a "baby-powder", a citrus fragrance, or a mixture of fragrances. The amount of fragrance used in each patch should be sufficient to mask foot odors for at least 8 hours or more and shoe odors for about one day to one week. Such amounts can range from about 10 mg to about 80 mg fragrance, preferably about 20 to about 70 mg fragrance, most preferably about 30 50 mg of fragrance per patch.

The fragrance can be entrapped into any suitable polymer which can be coated on the carrier or the fragrance can be incorporated into the carrier itself. Suitable polymers include those prepared from poly(vinyl pyrrolidone), acrylics or hydrogels. Polyvinylpyrrolidone (PVP) is a polymer that possesses unusual complexing and colloidal properties and is physiologically inert, as described in The Handbook of Water-Soluble Gums and Resins by Robert L. Davidson, Chapter 21—"Polyvinylpyrrolidone", McGraw-Hill, Inc. (1980), pp 21-1 to 21-21, whose preparative teachings are incorporated herein by reference. Hydrogels are materials derived from the interaction of polyvinylpyrrolidone with urethanes, giving a water swellable material which is slippery when wet. The polyvinylpyrrolidone in the hydrogel is capable of forming complexes with polar materials by hydrogen bonding and can form stable complexes with hydrophobic materials by van der Waals interactions. A commercially available hydrogel is known as Hydromers®, trademark of Hydromer Inc., Salem Industrial Park, U.S. Route 22, P.O. Box 337, Whitehouse, N.J. Such hydrogels can form excellent films on the carder even when blended with fragrance.

Preferably, a mixture of the fragrance and a suitable polymer such as polyvinyl pyrrolidone are added to the carrier. The fragrance/polymer mixture increases the viscosity of the fragrance, thus facilitating the application of the fragrance to the carrier. The mixture also enables the fragrance to associate with the carrier to give a triggered release, i.e. time, heat, moisture and pressure, depending upon the type of carrier employed. For example, the use of poly(vinyl pyrrolidone) can give a moisture-triggered release, where the fragrance associated with the polymer can be dispaced by water, thus releasing the fragrance. Other polymers or microencapsulation systems can give a temperature- or pressure-triggered release.

A tackifier is any substance which enhances the property of tack of a pressure sensitive adhesive. Suitable tackifiers include rosin acid derivatives, terpene based derivatives and synthetic C-5 tackifiers such as Escorez 1310 of the Exxon Corporation. The amount of tackifier in the adhesive can range from about 10 to about 60% by weight of the adhesive, preferably from about 20 to about 40%.

Polybutene is a known short chain oligimer which serves to plasticize the high molecular weight polyisobutene. The amount of polybutene in the adhesive can range from about 10 to about 40% by weight, preferably from about 20 to about 30%. For example a suitable polybutene is H-1500 of the Amoco Corporation.

Polyisobutylene is a known high molecular weight polymer or resin which serves as the primary structural component of the adhesive. The amount of polyisobutene in the adhesive can range from about 30 to about 80% by weight of the composition. Other ranges within the above range can vary, depending upon the amounts of tackifier and polybutene used.

Typically, the fragrance is incorporated into the carrier by blending or mixing the fragrance with a polymer and adding the fragrance/polymer mixture to the carrier. Any suitable solvent can be employed for mixing the fragrance with the polymer, including alcohols of such as methanol, ethanol and isopropanol, most preferably methanol. The solvent can be employed in amounts sufficient to solubilize the polymer and can range from about 30 to about 70 percent or more solvent, more preferably about 50 percent solvent.

To construct a moisture-triggered patch, the fragrance is blended into a suitable hydrophilic polymer. The fragrance binds to the hydrophilic polymer, but not as strongly as water would. When the complex is exposed to water, the fragrance is displaced and is free to evaporate to mask unpleasant foot or shoe odors.

The adhesive should be able to retain sufficient adhesion to the skin or foot surface following exposure to fragrance. One class of suitable pressure-sensitive adhesives includes those as described in U.S. Pat. No. 4,605,592 or European Patent Application 103407, whose preparative teachings are incorporated herein by reference. Preferably the adhesive is the reaction product of reactants comprising (i) acrylic acid and/or methacrylic acid and/or acrylamide, and/or methacrylamide, (ii) an alkylacrylate and/or alkylmethacrylate having at least 4 carbon atoms and wherein the carbon atom attached to the oxy atom of the crbonyloxy group has at least one hydrogen atom attached thereto, and (iii) at least one additional ethylenically unsaturated monomer.

In a narrower embodiment, the adhesive is the polymeric reaction product of reactants comprising i) one or more acid or amide selected from acrylic acid, methacrylic acid, acrylamide or methacrylamide;

ii) one or more esters selected from n-butyl acrylate, methylbutyl acrylate and iso-octyl acrylate; and iii) one or more additionally ethylenically unsaturated monomers selected from N-vinyl pyrrolidone, methyl acrylate and vinyl acetate.

Preferably, the adhesive is a terpolymer prepared from n-butylacrylate or methacrylate, N-vinyl pyrrolidone and acrylic acid. To evaluate adhesives, the patch can have a shear strength of about 10 minutes or greater, as measured by a modified pressure sensitive tape council method PSTC-7. In this method, the patch has a shear strength of about 10 minutes or greater when packaged for 3 month storage at 37° C. In an alternative method of evaluation, the adhesive should enable the patch to remain securely attached to the foot for at least an 8 hour period or to the shoe for about 24 hours to about one week. A preferred adhesive for the foot is 3M's F9465PC, from the Minnesota Mining and Manufacturing Company, St. Paul, Minn. Generally, the criteria for an adhesive for the foot (i.e. skin) will tend to be different from the criteria for an adhesive for the shoe. The thickness of the adhesive for the foot can range from about one to about six mils, preferably from about three to about five mils. Generally, an adhesive for the shoe will require a higher shear strength, lower peel and tack, and will be about one to two mils in thickness. The adhesive can be continuous or discontinuous on the surface of the patch.

A release liner should be used to prevent contamination of the adhesive prior to its contact with the foot or shoe. Suitable release liners include high density polyethylene (HDPE), polyester (i.e. Mylar ®), polyethylene terephthalate (PET) and the like, preferably 7 mil high density polyethylene film.

The patch can be formed into any convenient shape, such as ovals, squares, triangles, stars, animal-shaped, and the like. Preferably the patch is of a circular shape or disk-shaped, about 2 to 3 centimeters (cm) in diameter, preferably about 2.2 cm (⅞ inches).

The patches can be stored in any suitable container, such as in a pouch made of metalized polyester film or a foil paper or foil polymer laminate.

The following examples are intended to illustrate, but not limit the invention.

EXAMPLE 1

Preparation of moisture triggered, foot deodorizer patch

A 2.5 cm (one inch) diameter fragrance patch is prepared from the following:

| | |
|---|---|
| occlusive layer: | 1.5 mil polyethylene |
| carrier: | polypropylene felt coated with a mixture of polymer/fragrance: |
| | 33.3% baby powder fragrance |
| | 33.3% polyvinyl pyrrolidone |
| | 33.3% isopropanol |
| adhesive: | 2 mil of pressure sensitive adhesive: |
| | 40% high molecular weight polyisobutylene (PIB) |
| | 30% polybutene |
| | 30% C-5 tackifier |
| final product release liner: | 5 mil polyester |

The adhesive is prepared mixing the PIB, the polybutene and the C-5 tackifier in a heptane solvent until a homogeneous solution is obtained, coating the solution on a roll coater and drying the coated solution in a roll coater oven. The occlusive layer is sintered onto the polypropylene felt. The polyvinylpyrrolidone, the baby powder fragrance and isopropanol are blended to a viscosity of about 120 centipoise. The mixture is blended again for even dispersion of the fragrance and to release any air bubbles. The polyvinyl pyrrolidone/fragrance is coated onto the felt and the isopropanol is evaporated off to give a patch containing 48 mg of fragrance per patch. The adhesive is laminated to the occlusive layer following evaporation of the isopropanol. A temporary release liner is removed and the final product release liner is laminated to the adhesive. In a wear test, greater than 70 to 80 percent of the wearers retained their foot patch after 24 hours.

EXAMPLE 2

Preparation of moisture triggered, foot deodorizer patch

A 2.2 cm (⅞ inch) diameter fragrance patch is prepared from the following:

| | |
|---|---|
| carrier/non-occlusive: | 40 mil (8 oz/yd) polypropylene felt, partially sintered treated on one surface and coated on the non-sintered surface with a mixture of: 30% polyvinylpyrrolidone 30% baby powder fragrance 40% methanol |
| adhesive: | 5 mil 3M F9465 PC pressure sensitive adhesive |
| release liner: | 7 mil HDPE |

The polyvinylpyrrolidone, the baby powder fragrance and methanol are mixed as in Example 1. The mixture is coated onto the non-sintered surface of the felt carrier to give a fragrance loading of 11 mg/cm$^2$. The coated felt carrier is air dried for one hour, cut into 2.2 cm diameter patches containing 36 mg of fragrance per patch. The adhesive is laminated onto the sintered surface of the carrier. The temporary release liner is removed and the final product release liner is laminated to the adhesive. In a wear test, greater than 95 percent of the wearers retained their foot patch after 24 hours.

It is claimed:

1. A patch for masking foot and shoe odors, comprising:
    a) a non-occlusive layer
    b) a carrier on one side of the barrier layer and containing from about 10 milligrams to about 80 milligrams fragrance per patch;
    c) a pressure sensitive adhesive on the other side of the non-occlusive layer for securing said patch to a foot or shoe, such that the patch can mask foot and shoe odors through release of fragrance and still remain securely attached to the foot for at least an 8 hour period or to the shoe for at least a 24 hour period.

2. The patch of claim 1 wherein the carrier is polypropylene felt.

3. The patch of claim 1 wherein the barrier layer is integrated into the carrier.

4. The patch of claim 3 wherein the barrier layer is formed by sintering one side of the carrier.

5. The patch of claim 1 wherein the amount of fragrance ranges from about 30 to 50 milligrams of fragrance per patch.

6. The patch of claim 1 wherein the fragrance is coated onto the carrier with a mixture of polymer and fragrance.

7. The patch of claim 6 wherein the polymer is polyvinylpyrrolidone.

8. A method for masking foot and shoe odors, comprising, attaching to the foot or shoe, a patch comprising:
    a) a non-occlusive layer
    b) a carrier on one side of the non-occlusive layer and containing from about 10 milligrams to about 80 milligrams fragrance per patch;
    c) a pressure sensitive adhesive on the other side of the non-occlusive layer for securing said patch to a foot or shoe, such that the patch can mask foot and shoe odors through release of fragrance and still remain securely attached to the foot for at least an 8 hour period or to the shoe for at least a 24 hour period.

9. The method of claim 8 wherein the carrier is polypropylene felt.

10. The method of claim 8 wherein the non-occlusive layer is integrated into the carrier.

11. The method of claim 8 wherein the non-occlusive layer is formed by sintering one side of the carrier.

12. The method of claim 8 wherein the amount of fragrance ranges from about 30 to about 50 milligrams of fragrance per patch.

13. The method of claim 8 wherein the fragrance is coated onto the carrier with a mixture of polymer and fragrance.

14. The method of claim 13 wherein the polymer is polyvinylpyrrolidone.

* * * * *